(12) United States Patent
Kang et al.

(10) Patent No.: US 9,683,945 B2
(45) Date of Patent: Jun. 20, 2017

(54) APPARATUS AND METHOD FOR INSPECTING A FLEXIBLE GLASS RIBBON

(71) Applicant: Corning Incorporated, Corning, NY (US)

(72) Inventors: Kiat Chyai Kang, Painted Post, NY (US); Richard Sean Priestley, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 5 days.

(21) Appl. No.: 14/403,694

(22) PCT Filed: May 23, 2013

(86) PCT No.: PCT/US2013/042404
§ 371 (c)(1),
(2) Date: Nov. 25, 2014

(87) PCT Pub. No.: WO2013/181060
PCT Pub. Date: Dec. 5, 2013

(65) Prior Publication Data
US 2015/0160140 A1 Jun. 11, 2015

Related U.S. Application Data

(60) Provisional application No. 61/652,904, filed on May 30, 2012.

(51) Int. Cl.
*G01N 21/84* (2006.01)
*G01N 21/89* (2006.01)
(Continued)

(52) U.S. Cl.
CPC ............ *G01N 21/8914* (2013.01); *G01L 1/24* (2013.01); *G01N 21/896* (2013.01)

(58) Field of Classification Search
CPC .... G01N 21/86; G01N 21/89; G01N 21/8901; G01N 33/346; G01N 33/365
(Continued)

(56) References Cited

U.S. PATENT DOCUMENTS 4,306,808 A * 12/1981 Vander Neut ........ G01N 21/896
250/559.39
5,917,934 A * 6/1999 Chiu et al. .................... 382/149
(Continued)

FOREIGN PATENT DOCUMENTS

EP 24586 A1 8/1979
JP 2011144093 A 7/2011
(Continued)

OTHER PUBLICATIONS

Chinese First Office Action CN201380034655.4 Dated Aug. 23, 2016, Chinese Patent Office.
(Continued)

*Primary Examiner* — Tarifur Chowdhury
*Assistant Examiner* — Md M Rahman
(74) *Attorney, Agent, or Firm* — Jeffrey A. Schmidt

(57) ABSTRACT

An apparatus (10) is provided for inspecting a flexible glass ribbon. In one example, the apparatus includes at least one storage roll (16) for storing a length of the flexible glass ribbon (12). In another example, the apparatus further includes an inspection device (50). In yet another example, the inspection device can inspect a characteristic of an unrolled portion (28) of the flexible glass ribbon (12) spanning along a travel path (14) of the flexible glass ribbon.

20 Claims, 3 Drawing Sheets

(51) Int. Cl.
*G01L 1/24* (2006.01)
*G01N 21/896* (2006.01)

(58) Field of Classification Search
USPC .......................................................... 356/429
See application file for complete search history.

(56) References Cited

U.S. PATENT DOCUMENTS

| | | |
|---|---|---|
| 6,788,462 B2 | 9/2004 | Lesniak |
| 7,345,698 B2 | 3/2008 | Abbott et al. |
| 7,551,274 B1 | 6/2009 | Wornson et al. |
| 7,769,223 B2 | 8/2010 | Shinohara et al. |
| 7,883,778 B2 | 2/2011 | Nakamura et al. |
| 7,920,257 B2 | 4/2011 | An et al. |
| 8,120,654 B2 | 2/2012 | Okamura |
| 8,184,291 B2 | 5/2012 | Suzuki |
| 8,284,396 B2 | 10/2012 | Rudert |
| 2004/0057046 A1* | 3/2004 | Abbott ................. G01N 21/896 356/239.1 |
| 2004/0169809 A1 | 9/2004 | Yamabuchi et al. |
| 2006/0132735 A1* | 6/2006 | Lof ...................... G03F 7/70791 355/53 |
| 2007/0138228 A1* | 6/2007 | Brown ...................... B24B 9/10 226/97.1 |
| 2007/0140311 A1 | 6/2007 | House et al. |
| 2007/0165941 A1 | 7/2007 | Shinohara et al. |
| 2009/0288567 A1 | 11/2009 | Choi et al. |
| 2010/0031702 A1* | 2/2010 | Tomamoto ............ C03B 17/068 65/91 |
| 2011/0014445 A1 | 1/2011 | Hawtof |
| 2011/0154862 A1* | 6/2011 | Fukami ................ C03B 27/0404 65/104 |
| 2011/0222053 A1 | 9/2011 | Kamikawa et al. |
| 2012/0312457 A1* | 12/2012 | Hosoe ........................... 156/182 |
| 2013/0074549 A1* | 3/2013 | Ahrens ..................... C03B 17/06 65/29.21 |
| 2013/0126576 A1* | 5/2013 | Marshall ............... C03B 33/033 225/2 |

FOREIGN PATENT DOCUMENTS

| | | |
|---|---|---|
| JP | 2012236675 A | 12/2012 |
| JP | 2013-24713 A | 2/2013 |
| JP | 2013227169 A | 11/2013 |
| WO | 2010/079474 A1 | 7/2010 |
| WO | 2012/081503 A1 | 12/2011 |

OTHER PUBLICATIONS

Search Report from outside source; Dated Apr. 27, 2012; From Peame & Gordon LLP.
English Translation of JP2015515074 Office Action Dated Mar. 23, 2017, Japan Patent Office.

* cited by examiner

APPARATUS AND METHOD FOR INSPECTING A FLEXIBLE GLASS RIBBON

This application claims the benefit of priority of U.S. Provisional Application Ser. No. 61/652,904 filed on May 30, 2012 the content of which is relied upon and incorporated herein by reference in its entirety.

TECHNICAL FIELD

The invention relates to apparatus and methods for inspecting characteristics of glass and, more particular, to inspecting characteristics of flexible glass.

BACKGROUND

It is generally known to measure stress, warpage, and thickness in glass sheets used in the manufacture of display devices. For example, it is known to observe polarized light with cameras to determine stress. It is also known to observe reflections off a glass surface with a camera to determine warpage.

SUMMARY

The following presents a simplified summary of the disclosure in order to provide a basic understanding of some example aspects described in the detailed description. The accompanying drawings are included to provide a further understanding of principles of the invention, and are incorporated in and constitute a part of this specification. The drawings illustrate one or more embodiment(s), and together with the description serve to explain, by way of example, principles and operation of the invention. It is to be understood that various features disclosed in this specification and in the drawings can be used in any and all combinations. By way of non-limiting example the various features may be combined with one another as set forth in the following aspects:

According to a first aspect, there is provided an apparatus for inspecting a flexible glass ribbon, the apparatus comprising:

at least one storage roll configured to store a length of the flexible glass ribbon; and an inspection device configured to inspect a characteristic of an unrolled portion of the flexible glass ribbon spanning along a travel path of the flexible glass ribbon.

According to a second aspect, there is provided the apparatus of aspect 1, further including a plurality of rollers configured to guide the unrolled portion of the flexible glass ribbon along the travel path, the plurality of rollers being configured to create a predetermined tension in the unrolled portion of the flexible glass ribbon.

According to a third aspect, there is provided the apparatus of aspect 2, wherein the plurality of rollers are configured to stabilize an inspection region of the unrolled portion of the flexible glass ribbon, wherein the inspection device is configured to inspect the characteristic within the inspection region of the flexible glass ribbon.

According to a fourth aspect, there is provided the apparatus of any one of aspects 1-3, wherein the inspection device is configured to measure the characteristic comprising a stress characteristic of the unrolled portion of the flexible glass ribbon.

According to a fifth aspect, there is provided the apparatus of any one of aspects 1-4, wherein the inspection device is configured to measure the characteristic comprising a thickness of the unrolled portion of the flexible glass ribbon.

According to a sixth aspect, there is provided the apparatus of any one of aspects 1-5, wherein the inspection device is configured to measure the characteristic comprising a warp characteristic of the unrolled portion of the flexible glass ribbon.

According to a seventh aspect, there is provided the apparatus of any one of aspects 1-6, wherein the inspection device includes an optical device.

According to an eighth aspect, there is provided the apparatus of aspect 7, wherein the optical device includes at least one camera configured to inspect the characteristic of the unrolled portion of the flexible glass ribbon.

According to a ninth aspect, there is provided the apparatus of aspect 8, wherein the at least one camera comprises a camera array configured to inspect the characteristic along a width of the unrolled portion of the flexible glass ribbon extending transverse to the travel path.

According to a tenth aspect, there is provided the apparatus of aspect 8, further comprising a polarized light source configured to operate with the at least one camera to inspect the characteristic comprising a stress characteristic of the unrolled portion of the flexible glass ribbon.

According to an eleventh aspect, there is provided the apparatus of aspect 8, further comprising a measurement device configured to be observed by the camera to inspect the characteristic comprising a warp characteristic along a width of the unrolled portion of the flexible glass ribbon extending transverse to the travel path.

According to a twelfth aspect, there is provided the apparatus of any one of aspects 1-11, wherein the at least one storage roll includes a first storage roll configured to store a first length of the flexible glass ribbon and a second storage roll configured to store a second length of the flexible glass ribbon.

According to a thirteenth aspect, there is provided a method of inspecting a characteristic of a flexible glass ribbon, the method comprising the steps of:

(I) providing a first storage roll storing a first length of the flexible glass ribbon; and (II) inspecting a characteristic of an unrolled portion of the flexible glass ribbon spanning along a travel path of the flexible glass ribbon.

According to a fourteenth aspect, there is provided the method of aspect 13, further comprising the steps of:

stabilizing an inspection region of the unrolled portion of the flexible glass ribbon with a plurality of rollers while inspecting the characteristic within the inspection region of the unrolled portion of the flexible glass ribbon; and adjusting at least one of the plurality of rollers to place the unrolled portion of the flexible glass ribbon under a predetermined tension in the inspection region.

According to a fifteenth aspect, there is provided the method of aspect 13, further comprising the step of placing the unrolled portion of the flexible glass ribbon under a predetermined tension.

According to a sixteenth aspect, there is provided the method of any one of aspects 13-15, wherein step (II) includes inspecting the characteristic comprising a stress characteristic of the unrolled portion of the flexible glass ribbon.

According to a seventeenth aspect, there is provided the method of any one of aspects 13-16, wherein step (II) includes inspecting the characteristic comprising a thickness of the unrolled portion of the flexible glass ribbon.

According to an eighteenth aspect, there is provided the method of any one of aspects 13-17, wherein step (II) includes inspecting the characteristic comprising a warp characteristic of the unrolled portion of the flexible glass ribbon.

According to a nineteenth aspect, there is provided the method of any one of aspects 13-17, wherein step (II) includes operating an optical device to inspect the characteristic of the unrolled portion of the flexible glass ribbon.

According to a twentieth aspect, there is provided the method of any one of aspects 13-19, wherein step (II) includes exposing the unrolled portion of the flexible glass ribbon with polarized light while at least one camera inspects the characteristic comprising a stress characteristic of the unrolled portion of the flexible glass ribbon.

According to a twenty first aspect, there is provided the method of any one of aspects 13-20, wherein step (II) includes inspecting a measurement device relative to the unrolled portion of the flexible glass ribbon with at least one camera to inspect a warpage of the flexible glass ribbon.

According to a twenty second aspect, there is provided the method of any one of aspects 13-21, wherein step (I) further provides a second storage roll storing a second length of the flexible glass ribbon, and wherein step (II) is carried out while the unrolled portion travels along the travel path from the first storage roll to the second storage roll.

BRIEF DESCRIPTION OF THE DRAWINGS

These and other aspects are better understood when the following detailed description is read with reference to the accompanying drawings, in which.

DETAILED DESCRIPTION

Figure 1:
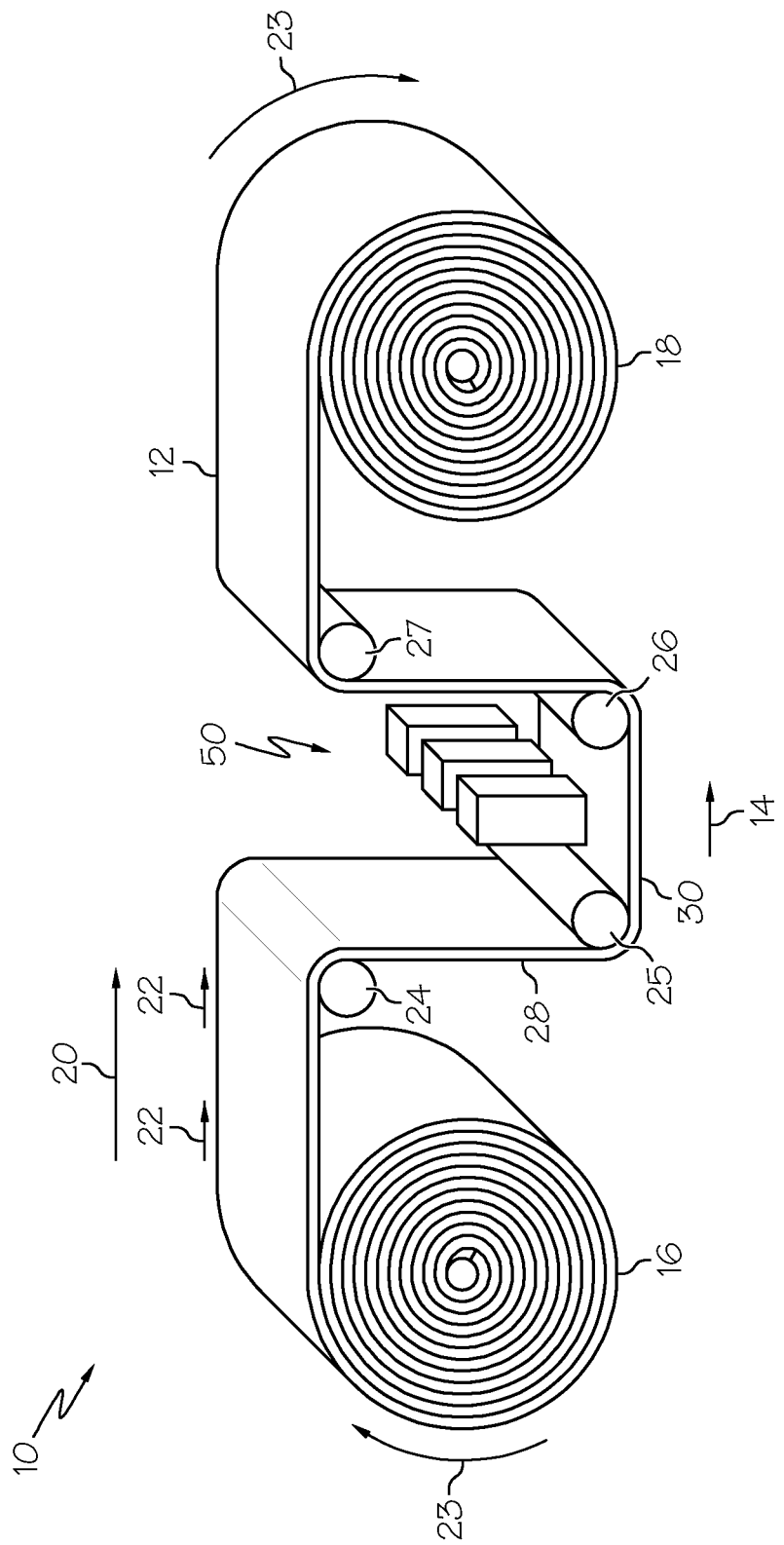
FIG. 1 is a perspective view of an example apparatus for inspecting a flexible glass ribbon in accordance with one aspect of the disclosure.

Examples will now be described more fully hereinafter with reference to the accompanying drawings in which example embodiments are shown. Whenever possible, the same reference numerals are used throughout the drawings to refer to the same or like parts. However, aspects may be embodied in many different forms and should not be construed as limited to the embodiments set forth herein.

FIG. 1 illustrates a perspective view of an apparatus 10 for inspecting a flexible glass ribbon 12 incorporating example aspects of the disclosure. In one example, the flexible glass ribbon 12 can be incorporated in roll to roll processing. The flexible glass ribbon may be wound with an interleaf between adjacent layers of the flexible glass in the roll, or may include other structure for keeping the surfaces of the flexible glass ribbon from touching one another. The flexible glass ribbon 12 may subsequently be unrolled from at least one roll to be scored and separated into sheets that may be used in a wide variety of applications. If an interleaf or other protective structure is present, such may be removed before the flexible glass ribbon is separated into sheets. For example, the separated glass sheets may be used as shields to protect a surface and/or as hermetic barriers to minimize the passage of air and/or water vapor in organic light-emitting diode (OLED) displays or photovoltaic (PV) applications. In further examples, the separated sheets may be incorporated into flexible displays or other applications. The flexible glass ribbon 12 can include a wide range of dimensions (e.g., length, width, thickness, etc.). As such, the flexible glass ribbon 12 shown in FIG. 1 includes a variety of sizes and shapes.

The apparatus 10 can include at least one storage roll. The at least one storage roll can store a length of the flexible glass ribbon 12. The flexible glass ribbon 12 can span along a travel path 14 extending from the length of the flexible glass ribbon 12 that is stored on the at least one storage roll. In one example, the at least one storage roll includes a single storage roll (e.g., the first storage roll 16 or the second storage roll 18). In further examples, the flexible glass ribbon 12 can extend between a first storage roll 16 and a second storage roll 18. As such, one end of the flexible glass ribbon 12 can optionally be supported by the first storage roll 16 while an opposing second end of the flexible glass ribbon 12 can optionally be supported by the second storage roll 18. In between the storage rolls 16 and 18, if present, an interleaf material can be removed from the flexible glass ribbon 12 upon unwinding from storage roll 16 and then re-introduced before the flexible glass ribbon is wound on storage roll 18.

The first storage roll 16 can store a first length of the flexible glass ribbon 12. For example, the first length of the flexible glass ribbon 12 can be wound around the first storage roll 16. Accordingly, the first storage roll 16 can be rotated in a direction such that flexible glass ribbon 12 can unwind from the first storage roll 16. In the shown example, the first storage roll 16 can be rotated in a clockwise direction 23 to cause the flexible glass ribbon 12 to unwind from the first storage roll 16 and span from the first storage roll 16 to the second storage roll 18. In further examples, the first storage roll 16 could be rotated in a counterclockwise direction instead to cause the flexible glass ribbon 12 to wind onto the first storage roll 16. Optionally, the first storage roll 16 may comprise a spool including flanges, or other similar structures to assist in maintaining the flexible glass ribbon 12 on the first storage roll 16.

The apparatus 10 can further include the optional second storage roll 18 spaced apart from the first storage roll 16. The second storage roll 18 can store a second length of the flexible glass ribbon 12. For example, the second length of the flexible glass ribbon 12 can be wound around the second storage roll 18. The second storage roll 18 can be similar in size and shape to the first storage roll 16, though, in other examples, the first storage roll 16 and second storage roll 18 could have different sizes and shapes. The second storage roll 18 can receive the flexible glass ribbon 12 from the first storage roll 16. In particular, the second storage roll 18 can be rotated in a direction such that the flexible glass ribbon 12 can wind onto the second storage roll 18. In the shown example, the second storage roll 18 can be rotated in the clockwise direction 23 to cause the flexible glass ribbon 12 to wind onto the second storage roll 18. In further examples, the second storage roll 18 can be rotated in a counterclockwise direction instead to cause the flexible glass ribbon 12 to unwind from the second storage roll 18. As with the first storage roll 16, the second storage roll 18 can optionally comprise a spool including flanges, or other similar structures to assist in maintaining the flexible glass ribbon 12 on the second storage roll 18.

The first storage roll 16 is not limited to unwinding and/or feeding the flexible glass ribbon 12. Similarly, the second storage roll 18 is not limited to winding and/or receiving the flexible glass ribbon 12. Instead, in further examples, the first storage roll 16 and second storage roll 18 can function in an opposite manner. In such an example, the first storage roll 16 can be wound to receive the flexible glass ribbon 12 while the second storage roll 18 can be unwound to feed the flexible glass ribbon 12. As such, the flexible glass ribbon 12 can move from the second storage roll 18 to the first storage roll 16.

The first storage roll 16 and second storage roll 18 can be rotated such that the flexible glass ribbon 12 can span along the travel path 14. The travel path 14 can extend from the first storage roll 16 to the second storage roll 18. In one example, the travel path 14 can extend from the first length of the flexible glass ribbon 12 that is stored on the first storage roll 16 to the second length of the flexible glass ribbon 12 that is stored on the second storage roll 18. In one example, the first length of the flexible glass ribbon 12 stored on the first storage roll 16 can be the same as or different from the second length of the flexible glass ribbon 12 stored on the second storage roll 18. For example, in some examples, the flexible glass ribbon can unwind from one storage roll at a different rate than it winds on the other storage roll.

In some examples, the first storage roll 16 and second storage roll 18 can rotate such that the flexible glass ribbon 12 can have continuous movement 20 (shown generally with continuous arrowhead). To have continuous movement 20, the first storage roll 16 can rotate continuously to cause the flexible glass ribbon 12 to unwind. By rotating continuously, the flexible glass ribbon 12 can move without hesitations, stops, for example, over a period of time. In one example, continuous movement 20 may or may not include continuous speed. For example, the first storage roll 16 can rotate continuously while maintaining a constant speed, such that the flexible glass ribbon 12 has continuous movement 20. In another example, the first storage roll 16 can rotate continuously while having a varying speed (e.g., speeding up or slowing down), such that the flexible glass ribbon 12 has continuous movement 20 while moving at varying speeds. In some examples, the first storage roll 16 and second storage roll 18 can rotate simultaneously, such that a speed of the flexible glass ribbon 12 unwinding from the first storage roll 16 can substantially match a speed of the flexible glass ribbon 12 winding on the second storage roll 18. However, in further examples, the first storage roll 16 and second storage roll 18 could rotate at different speeds, for example by having the second storage roll 18 rotating slower or not rotating with respect to the first storage roll 16.

The first storage roll 16 and second storage roll 18 are not limited to rotating such that the flexible glass ribbon 12 has continuous movement 20. For instance, the first storage roll 16 and the second storage roll 18 can rotate such that the flexible glass ribbon 12 has an indexing movement 22 (shown generally with an indexing arrowhead). To have indexing movement 22, the first storage roll 16 may not rotate continuously but, rather, may rotate intermittently. By rotating intermittently, the first storage roll 16 can rotate for a predetermined time, then stop rotating for a second predetermined time, then resume rotating for a third predetermined time, etc. Accordingly, the flexible glass ribbon 12 may not rotate continuously but, rather, can rotate a certain angular distance, then stop, then rotate through another angular distance, then stop, etc. In some examples, the first storage roll 16 and second storage roll 18 may not rotate simultaneously although the storage rolls may rotate at different times in further examples. As such, the second storage roll 18 could rotate slower or less frequently with respect to the first storage roll 16.

Referring still to FIG. 1, the apparatus 10 can further include one or more rollers. In the shown example, the apparatus 10 can include a plurality of rollers having a first pair of rollers, including a first roller 24 and a fourth roller 27, and a second pair of rollers, including a second roller 25 and a third roller 26. The rollers 24-27 can guide an unrolled portion 28 of the flexible glass ribbon 12 along the travel path 14. The rollers 24-27 can each include an elongated, cylindrically shaped structure extending across a width of the flexible glass ribbon 12 in a direction that is substantially transverse to the travel path 14. The rollers 24-27 can engage the unrolled portion 28 of the flexible glass ribbon 12 and move so that its circumferential speed matches the travel speed of the flexible glass ribbon 12. As such, the unrolled portion 28 of the flexible glass ribbon 12 can be guided by the rollers 24-27. The rollers 24-27 may have a surface producing low friction with respect to the flexible glass ribbon 12. The rollers 24-27 can include any number of sizes, shapes, and configurations. For example, the rollers 24-27 can each define a substantially smooth outer surface, grooved outer surface, or other surface configurations. In other examples, the rollers 24-27 could include one or more coatings or the like. In further examples, the rollers 24-27 could include drive units, motors, etc. to assist in rotating the rollers 24-27.

The first pair of rollers can include the first roller 24 and the fourth roller 27, for example. The first roller 24 is positioned in closer proximity to the first storage roll 16 than the remaining rollers. The fourth roller 27 is positioned in closer proximity to the second storage roll 18 than the remaining rollers. The first roller 24 and fourth roller 27 can be positioned above the second pair of rollers 25, 26, as shown, or may be disposed below the second pair or rollers 25, 26. The first roller 24 can guide the unrolled portion 28 of the flexible glass ribbon 12 along a bend, for example a substantially 90° bend. Similarly, the fourth roller 27 can also guide the unrolled portion 28 of the flexible glass ribbon 12 along a bend, for example a substantially 90° bend. In further examples, the first roller 24 and fourth roller 27 could guide the unrolled portion 28 along a varying degree of bends that may be greater or less than the 90° bend shown.

The second pair of rollers can include the second roller 25 and the third roller 26, for example. The second roller 25 and the third roller 26 can be positioned between the first roller 24 and fourth roller 27 along the travel path 14. In particular, the unrolled portion 28 of the flexible glass ribbon 12 can first engage the first roller 24, followed by engaging the second roller 25 and third roller 26, then engaging the fourth roller 27. The second roller 25 can guide the unrolled portion 28 of the flexible glass ribbon 12 along a bend, for example, a generally 90° bend. Similarly, the third roller 26 can also guide the unrolled portion 28 of the flexible glass ribbon 12 along a bend, for example, a generally 90° bend. In further examples, the second roller 25 and third roller 26 can guide the unrolled portion 28 along a varying degree of bends that may be greater or less than the 90° bend shown.

The rollers 24-27 can be arranged to create a predetermined tension in the unrolled portion 28 of the flexible glass ribbon 12, with the rotational speed of roll 16, the rotational speed of roll 18, and the relative positions of rolls 16 and 18, being maintained relatively constant. By bending around the rollers 24-27, the flexible glass ribbon 12 can be held so as to have a desired predetermined tension. This tension can, for example, be adjusted to substantially match a tension that the flexible glass ribbon will experience during subsequent roll to roll processing. In further examples, the tension in the flexible glass ribbon 12 can be adjusted so as to match a varying range of tensions that flexible glass ribbon may experience during roll to roll processing. In one example, the rollers 24-27 can be moved to adjust the tension in the unrolled portion 28. For instance, the second roller 25 and third roller 26 can be selectively moved. In one example, either or both of the second roller 25 and third roller 26 can be moved closer together or farther apart to respectively decrease or increase the tension in the flexible glass ribbon 12. In yet another example, either or both of the second roller 25 and third roller 26 can be moved towards or away from the first roller 24 and fourth roller 27 to respectively decrease or increase the tension in the flexible glass ribbon 12. In other examples, the first roller 24 and/or the fourth roller 27 can be moved with respect to the second roller 25 and third roller 26 to adjust the tension. As such, the predetermined tension in the unrolled portion 28 of the flexible glass ribbon 12 can be adjusted in a number of different ways, including by moving one or more of the first roller 24, second roller 25, third roller 26, and fourth roller 27. Alternatively, or in addition thereto, the relative rotational speed of the roller pairs may be set so as to produce a predetermined desired amount of tension in the ribbon 12. For example, roller 26 may be rotated at a slightly higher rotational speed than that of the roller 25 so as to produce tension in the segment of the glass ribbon 12 located between the rollers 25 and 26. A similar arrangement of roller speeds may be used between any two of the rollers 24, 25, 26, 27 so as to tension the glass ribbon 12 disposed therebetween. By producing a predetermined desired amount of tension in the portion of the glass ribbon 12 extending between any two of the rollers 24, 25, 26, 27, variations in ribbon speed and vibrations in the ribbon 12 outside of that ribbon portion extending between those two rollers may be isolated from that portion of the glass ribbon 12.

The second roller 25 and third roller 26 can be spaced apart from each other to guide the unrolled portion 28 of the flexible glass ribbon 12 along the travel path 14. In one example, the rollers 24-27 can stabilize and/or provide tension in an inspection region 30 of the unrolled portion 28 of the flexible glass ribbon 12. In the shown example, the inspection region 30 of the unrolled portion 28 can be located between the second roller 25 and third roller 26. However, in other examples, the inspection region 30 can be located at nearly any location along the unrolled portion 28 between the first storage roll 16 and the second storage roll 18. For example, the inspection region 30 of the unrolled portion 28 of the flexible glass ribbon 12 could be located between the first storage roll 16 and the first roller 24. In this case, storage roll 16 and first roller 24 become a roller pair that may be used as described above to produce tension in the glass ribbon extending therebetween. In another example, the inspection region 30 of the unrolled portion 28 of the flexible glass ribbon 12 could be located between the first roller 24 and the second roller 25. In yet another example, the inspection region 30 of the unrolled portion 28 of the flexible glass ribbon 12 could be located between the third roller 26 and the fourth roller 27. In a further example, the inspection region 30 of the unrolled portion 28 of the flexible glass ribbon 12 could be located between the fourth roller 27 and the second storage roll 18.

Referring still to FIG. 1, the apparatus 10 can further include an inspection device 50. The inspection device 50 can inspect characteristics within the inspection region 30 of the flexible glass ribbon 12. In one example, the inspection device 50 can include an optical device. As will be described in more detail below, the characteristics inspected can include, but are not limited to, a thickness of the unrolled portion 28 of the flexible glass ribbon 12. In another example, the characteristics inspected can include a stress characteristic of the unrolled portion 28 of the flexible glass ribbon 12. In yet another example, the characteristics inspected can include a warp characteristic of the unrolled portion 28 of the flexible glass ribbon 12. In further examples, however, the characteristics inspected are not limited to the thickness, stress, or warp of the unrolled portion 28, and can include any number of qualities or characteristics of the flexible glass ribbon 12.

The inspection device 50 is somewhat generically depicted in FIG. 1. Indeed, the inspection device 50 can include any number of different structures that can measure characteristics within the inspection region 30 of the flexible glass ribbon 12. For instance, in one example, the inspection device 50 comprises one or more sensors. The sensors are not limited to being placed above the inspection region 30, and, instead, could be positioned laterally adjacent the inspection region 30, below the inspection region 30, etc. The sensors can measure characteristics of the inspection region 30 including the thickness of the inspection region 30. In particular, the flexible glass ribbon 12 can be moved, for example by continuous movement 20 or indexing movement 22 with respect to the sensors. As such, the sensors can therefore measure the thickness or other characteristics along the length of the unrolled portion 28 of the flexible glass ribbon 12. In further examples, by extending across a width of the flexible glass ribbon 12, the sensors can also measure the thickness or other characteristics across the width of the unrolled portion 28 of the flexible glass ribbon 12. As shown, the inspection device 50 can allow for simultaneous monitoring of a characteristic along a width of the flexible glass ribbon 12. As such, a characteristic profile along the width of the flexible glass ribbon 12 can be intermittently or continuously monitored as the flexible glass ribbon 12 indexes or moves continuously along the travel path 14.

Figure 2:
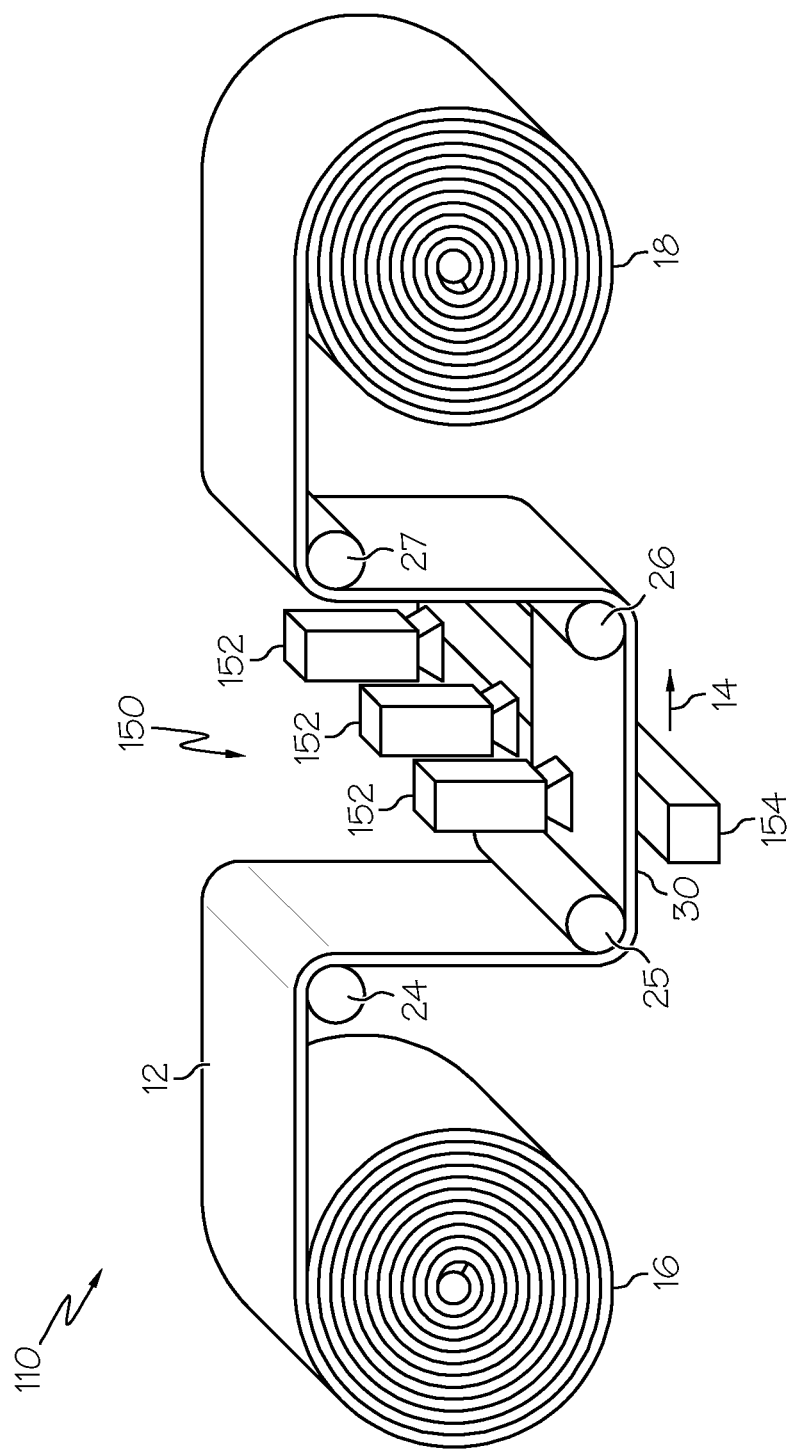
FIG. 2 is a perspective of a second example apparatus for inspecting the flexible glass ribbon including an example camera array and light source.

Referring now to FIG. 2, a second example of an apparatus 110 for inspecting the flexible glass ribbon 12 is shown. In this example, the apparatus 110 can include at least some of the structures of the apparatus 10 shown in FIG. 1. For example, the apparatus 110 can include the flexible glass ribbon 12, the first storage roll 16 and second storage roll 18, and the rollers 24-27. These structures can be similar or identical to the structures shown and described with respect to FIG. 1.

The apparatus 110 can include a second example of an inspection device 150. The inspection device 150 can inspect a characteristic of the unrolled portion 28 of the flexible glass ribbon 12 spanning along the travel path 14. In this example, the inspection device 150 can include an optical device. The optical device can include at least one camera for inspecting the characteristic of the unrolled portion 28 of the flexible glass ribbon 12.

The at least one camera can comprise a camera array 152. The camera array 152 is somewhat generically depicted for illustrative purposes, as the camera array 152 can include any number of configurations. In one example, the camera array 152 can include one or more line scan cameras for measuring two dimensional stress. While the camera array 152 is shown to include three cameras, the camera array 152 could include one or any number of cameras. The camera array 152 can inspect the characteristic of the unrolled portion 28 of the flexible glass ribbon 12. The camera array 152 can be positioned to extend across a width of the unrolled portion 28 in a direction that is substantially transverse to the travel path 14. Accordingly, the camera array 152 can inspect the characteristic at the inspection region 30 along the width of the unrolled portion 28. The camera array 152 is not limited to extending transverse to the travel path 14 and, in further examples, could extend along the travel path 14 (e.g., along the length of the flexible glass ribbon 12). Similarly, while the camera array 152 is shown to form a substantially linear row, the camera array 152 is not so limited. Rather, the camera array 152 could also be staggered (i.e., form a non-linear path). Further, the camera array 152 could comprise a plurality of rows that could be parallel to each other or staggered. Providing the camera array 152 can allow for simultaneous monitoring of a characteristic along a width of the flexible glass ribbon 12. As such, a characteristic profile along the width of the flexible glass ribbon 12 can be intermittently or continuously monitored as the flexible glass ribbon 12 indexes or moves continuously along the travel path 14.

The inspection device 150 can further include a light source 154. The light source 154 can be positioned on a side of the flexible glass ribbon 12 that is opposite from the side along which the camera array 152 extends. In one example, the light source 154 can be positioned below the flexible glass ribbon 12 while the camera array 152 is positioned above the flexible glass ribbon 12. The light source 154 can extend along the inspection region 30 between the second roller 25 and the third roller 26. In particular, the light source 154 can be positioned to extend across a width of the unrolled portion 28 in a direction that is substantially transverse to the travel path 14. As such, the light source 154 can extend in a direction that is parallel with respect to the direction along which the camera array 152 extends. The light source 154 can be spaced apart from the flexible glass ribbon 12 and, in one example, can be aligned at normal incidence to the flexible glass ribbon 12.

The light source 154 can operate with the at least one camera, including the camera array 152 to inspect the characteristic comprising a stress characteristic, for example residual stress, of the unrolled portion 28 of the flexible glass ribbon 12. The light source 154 can direct light through the inspection region 30 of the unrolled portion 28 towards the camera array 152. In one example, the light source 154 comprises a polarized light source. As such, the light from the light source 154, which may include polarized light, can be received by the camera array 152. The state of the light received by the camera array 152 can then be analyzed, for example by detecting a change in polarization, to measure stress within the inspection region 30 of the unrolled portion 28. For example, the polarization of the light passing through the flexible glass ribbon 12 can change in its polarization state, which can be inspected by the camera array 152. These changes to the polarized light can occur due to residual stress in the flexible glass ribbon 12. The camera array 152 can include a linear pixel array with an optical polarizer mounted in front of the array for analyzing an optical state of the polarized light.

Because the camera array 152 and light source 154 extend across the width of the flexible glass ribbon 12, the stress characteristic of a cross-sectional portion of the unrolled portion 28 can be inspected. However, since the flexible glass ribbon 12 moves along the travel path 14 (e.g., continuously or indexed) with respect to the inspection device 150, the camera array 152 can also measure stress characteristics along the length of the unrolled portion 28 as well. A stress profile can therefore be generated of the flexible glass ribbon 12 along the width of the flexible glass ribbon 12. The stress profile can be generated intermittently and/or continuously.

Figure 3:
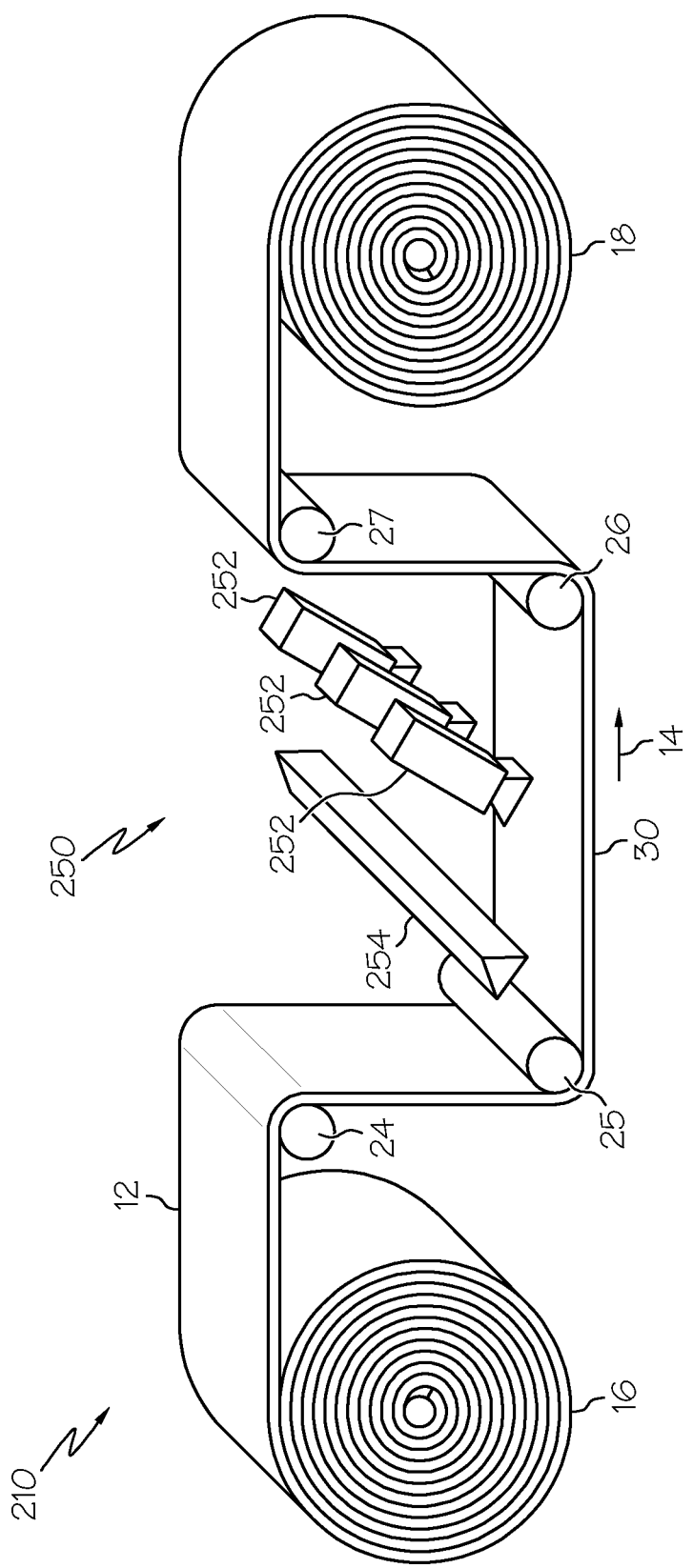
FIG. 3 is a perspective view of a third example apparatus for inspecting the flexible glass ribbon including a second example camera array and a measurement device.

Referring now to FIG. 3, a third example of an apparatus 210 for inspecting the flexible glass ribbon 12 is shown. In this example, the apparatus 210 can include at least some of the features of the apparatus 10 shown in FIG. 1. For example, the apparatus 210 can include the flexible glass ribbon 12, the first storage roll 16 and second storage roll 18, and the rollers 24-27. These structures can be similar or identical to the structures shown and described with respect to FIGS. 1 and 2.

The apparatus 210 can include a third example of an inspection device 250. The inspection device 250 can inspect a characteristic of the unrolled portion 28 of the flexible glass ribbon 12 spanning along the travel path 14. In this example, the inspection device 250 can include an optical device. The optical device can include at least one camera for inspecting the characteristic of the unrolled portion 28 of the flexible glass ribbon 12.

The at least one camera can comprise a camera array 252. The camera array 252 is somewhat generically depicted for illustrative purposes, as the camera array 252 can include any number of configurations. For example, while the camera array 252 is shown to include three cameras, the camera array 252 could include as few as one or more cameras. The camera array 252 can inspect the characteristic of the unrolled portion 28 of the flexible glass ribbon 12. The camera array 252 can be positioned to extend across a width of the unrolled portion 28 in a direction that is substantially transverse to the travel path 14. Accordingly, the camera array 252 can inspect the characteristic at the inspection region 30 along the width of the unrolled portion 28. The camera array 252 is not limited to extending transverse to the travel path 14 and, in further examples, could extend along the travel path 14. Similarly, while the camera array 252 is shown to form a substantially linear row, the camera array 252 could be staggered (i.e., form a non-linear path) or could form a plurality of rows that may be parallel or staggered. In one example, the camera array 252 may include a charge-coupled device (CCD) camera for measuring warp characteristics.

The inspection device 250 can further include a measurement device 254. The measurement device 254 is somewhat generically depicted for illustrative purposes, as the measurement device 254 can include any number of structures. The measurement device 254 can be positioned on the same side of the flexible glass ribbon 12 as the camera array 252. The measurement device 254 can be spaced apart a distance from the flexible glass ribbon 12 and can extend across the width of the unrolled portion 28 at the inspection region 30. In particular, the measurement device 254 can extend in a direction that is substantially transverse to the travel path 14. In further examples, however, the position of the measurement device 254 is not so limited, and could extend only partially along the width of the unrolled portion 28. In another example, the measurement device 254 could extend along the length of the unrolled portion 28.

In operation, the measurement device 254 can be observed by the camera array 252 to inspect the characteristic comprising a warp characteristic along the width of the unrolled portion 28 of the flexible glass ribbon 12. For example, the camera array 252 can be focused on the unrolled portion 28 and can capture the image of the measurement device 254 that reflects off the flexible glass ribbon 12. This reflection of the measurement device 254 can be analyzed to measure warpage of the flexible glass ribbon 12. In particular, the reflection of the measurement device 254 can be compared to a reference image that reflects off the flexible glass ribbon 12 if the flexible glass ribbon 12 were substantially smooth. In a further example, a straight edge analysis can be performed on the captured data (e.g., reflection of the measurement device 254) using image analysis routines to determine deviation from straight and the corresponding Z-shape of the flexible glass ribbon 12. Accordingly, the inspection device 250 can inspect the characteristic comprising a warp characteristic along a width of the unrolled portion 28. Further, since the flexible glass ribbon 12 moves along the travel path 14 (e.g., continuously or indexed) with respect to the inspection device 250, the camera array 252 can also measure warp characteristics along the length of the unrolled portion 28 as well. A profile of the warp characteristics of the flexible glass ribbon 12 can therefore be generated across either or both of the length and width.

The inspection device 250 is not limited to the camera array 252 and measurement device 254 for measuring warp characteristics of the flexible glass ribbon 12. In further examples, the inspection device 250 could include a wide range of devices for measuring warpage. For instance, the inspection device 250 could include one or more sensors that are spaced a distance from a surface of the inspection region 30 of the unrolled portion 28. The sensors could extend across a length or width of the unrolled portion 28. In this example, the sensors can measure a distance from the sensors to the flexible glass ribbon 12. This distance can be compared to a reference distance from the sensors to the flexible glass ribbon 12 if the flexible glass ribbon 12 were substantially flat. Accordingly, the sensors can determine warpage in the flexible glass ribbon 12 based on this distance comparison. Since the flexible glass ribbon 12 moves along the travel path 14, the profile of the warp characteristics of the flexible glass ribbon 12 can therefore be generated.

A method of inspecting the characteristics of the flexible glass ribbon 12 will now be described with respect to FIGS. 1 to 3. Similar or identical method steps may be formed with further examples, for instance, as described throughout the application. Moreover, example methods of the present disclosure may omit and/or add additional steps. Unless noted, the steps can be performed simultaneously, sequentially, or in different orders depending on the particular application.

Referring to FIG. 1, the method of inspecting a characteristic of the flexible glass ribbon 12 includes the step of providing at least one storage roll for storing a length of the flexible glass ribbon 12. Further, the method includes the step of inspecting a characteristic of the unrolled portion 28 of the flexible glass ribbon 12 spanning along the travel path 14 extending from the length of the flexible glass ribbon 12. The unrolled portion 28 of the flexible glass ribbon 12 may be maintained under tension. The method can further include the step of operating the optical device to inspect the characteristic of the unrolled portion 28 of the flexible glass ribbon 12.

Referring to FIG. 2, the method of inspecting a characteristic of the flexible glass ribbon 12 further includes the step of inspecting a stress characteristic of the unrolled portion 28 of the flexible glass ribbon 12. In one example, the inspection device 150 can include the camera array 152 and the light source 154. The method includes the step of exposing the unrolled portion 28 of the flexible glass ribbon 12 with light from the light source 154, for example polarized light, while at least one camera from the camera array 152 inspects the characteristic comprising a stress characteristic of the unrolled portion 28 of the flexible glass ribbon 12.

Referring now to FIG. 3, the method of inspecting a characteristic of the flexible glass ribbon 12 can also include the step of inspecting a warp characteristic of the unrolled portion 28 of the flexible glass ribbon 12. In this example, the inspection device 250 can include the camera array 252 and the measurement device 254. The method includes the step of inspecting the unrolled portion 28 of the flexible glass ribbon 12 with at least one camera from the camera array 252 to inspect the warpage of the flexible glass ribbon 12.

Referring now to FIGS. 1 to 3, the method further includes the step of providing the at least one storage roll as comprising the first storage roll 16 for storing the first length of the flexible glass ribbon 12. The at least one storage roll may further include the second storage roll 18 for storing the second length of the flexible glass ribbon 12. The method step of inspecting the characteristic of the flexible glass ribbon 12 can be carried out while the unrolled portion 28 travels along the travel path 14 from the first storage roll 16 to the second storage roll 18. Indeed, as depicted in FIG. 1, the flexible glass ribbon 12 can have continuous movement 20 or, in the alternative, indexing movement 22.

The method further includes the step of stabilizing and/or placing the flexible glass ribbon 12 in tension in the inspection region 30 of the unrolled portion 28 of the flexible glass ribbon 12. The inspection region 30 can be stabilized, for example, with the plurality of rollers 24-27. During the stabilization of the inspection region 30, the characteristic within the inspection region 30 of the unrolled portion 28 of the flexible glass ribbon 12 can be inspected. The method includes the step of creating a predetermined tension in the inspection region 30 of the unrolled portion 28. At least one of the plurality of rollers 24-27 can be adjusted to create a predetermined tension in the inspection region 30 of the unrolled portion 28 of the flexible glass ribbon 12. For example, the second roller 25 and/or the third roller 26 could be moved closer together or farther apart to adjust the tension in the inspection region 30.

Providing tension can allow the inspection region 30 to model stress conditions in a subsequent process (e.g., roll to roll) to allow for analysis of various characteristic (e.g., warpage, stress, glass thickness, etc.) associated with the flexible glass ribbon 12 being processed under such conditions. Aspects of the disclosure can therefore be used in some examples to test the flexible glass ribbon 12 for product quality and/or to help modify manufacturing conditions to address undesirable characteristics of the flexible glass ribbon 12 under tension.

In another example embodiment, the storage roll on the upstream side of the glass ribbon conveyance may be replaced by a forming process for making the glass ribbon. For example, the forming process may comprise a fusion down-draw process although other glass forming process may be provided in further examples. As such, the roller configuration and techniques described above may be used in an on-line inspection method whereby the ribbon is inspected as it is produced downstream from the glass forming process. In this instance, an unrolled portion of the glass ribbon may be one that has not yet been rolled.

The ribbon of the various embodiments herein can have a wide range of thicknesses. For example, the flexible glass ribbon may have a thickness of from about 50 µm to about 300 µm, and may be made of any suitable glass composition. In one example, Corning's Eagle XG™ alkali-free boro-alumino-silicate glass may be used although other glass compositions may be used in further examples.

The invention has been described with reference to the example embodiments described above. Modifications and alterations will occur to others upon a reading and understanding of this specification. Examples embodiments incorporating one or more claims of the invention are intended to include all such modifications and alterations insofar as they come within the scope of the appended claims.

What is claimed is:

1. An apparatus for inspecting a flexible glass ribbon, the apparatus comprising:
   at least one storage roll configured to store a length of the flexible glass ribbon;
   a plurality of rollers with a first roller of the plurality of rollers being adjustable to be moved closer to or farther away from a second roller of the plurality of rollers to adjust a tension in an inspection region of an unrolled portion of the flexible glass ribbon spanning between the first roller and the second roller; and
   an optical device positioned and configured to inspect a characteristic of a glass portion of the unrolled portion of the flexible glass ribbon within the inspection region between the first roller and the second roller.

2. The apparatus of claim 1, wherein the plurality of rollers are configured to stabilize the inspection region of the unrolled portion of the flexible glass ribbon.

3. The apparatus of claim 1, wherein the optical device includes at least one camera configured to inspect the characteristic of the glass portion of the unrolled portion of the flexible glass ribbon.

4. The apparatus of claim 3, wherein the at least one camera comprises a camera array configured to inspect the characteristic along a width of the unrolled portion of the flexible glass ribbon extending transverse to the travel path.

5. The apparatus of claim 3, further comprising a polarized light source configured to operate with the at least one camera to inspect the characteristic comprising a stress characteristic of the glass portion of the unrolled portion of the flexible glass ribbon.

6. The apparatus of claim 3, further comprising an elongated member at least extending in a direction that is substantially transverse to the travel path, wherein the elongated member is configured to extend at least partially along a width of the unrolled portion of the flexible glass ribbon extending transverse to the travel path, and wherein the elongated member is configured to be observed by the camera to inspect the characteristic comprising a warp characteristic along the width of the unrolled portion.

7. The apparatus of claim 1, wherein the at least one storage roll includes a first storage roll configured to store a first length of the flexible glass ribbon and a second storage roll configured to store a second length of the flexible glass ribbon.

8. The apparatus of claim 1, wherein the optical device is configured to measure the characteristic comprising a stress characteristic, thickness, or warp, of the glass portion in the inspection region of the unrolled portion of the flexible glass ribbon.

9. A method of inspecting a characteristic of a glass portion of a flexible glass ribbon, the method comprising the steps of:
   (I) providing a first storage roll storing a first length of the flexible glass ribbon; and
   (II) inspecting a characteristic of the glass portion of an unrolled portion of the flexible glass ribbon spanning along a travel path of the flexible glass ribbon;
   (III) stabilizing an inspection region of the unrolled portion of the flexible glass ribbon with a plurality of rollers while inspecting the characteristic within the inspection region of the unrolled portion of the flexible glass ribbon; and
   (IV) adjusting at least one of the plurality of rollers to adjust a tension of the unrolled portion of the flexible glass ribbon in the inspection region, wherein the step of adjusting includes moving a first roller of the plurality of rollers closer to or farther away from a second roller of the plurality of rollers to adjust the tension in the inspection region, wherein the inspection region spans between the first roller and the second roller.

10. The method of claim 9, wherein step (II) includes inspecting the characteristic comprising a stress characteristic, thickness, or warp, of the glass portion of the unrolled portion of the flexible glass ribbon.

11. The method of claim 9, wherein step (II) includes operating an optical device to inspect the characteristic of the glass portion of the unrolled portion of the flexible glass ribbon.

12. The method of claim 9, wherein step (II) includes exposing the glass portion of the unrolled portion of the flexible glass ribbon with polarized light while at least one camera inspects the characteristic comprising a stress characteristic of the glass portion of the unrolled portion of the flexible glass ribbon.

13. The method of claim 9, wherein step (II) includes inspecting an elongated member relative to the unrolled portion of the flexible glass ribbon with at least one camera to inspect a warpage of the glass portion of the flexible glass ribbon.

14. The method of claim 9, wherein step (I) further provides a second storage roll storing a second length of the flexible glass ribbon, and wherein step (II) is carried out while the unrolled portion travels along the travel path from the first storage roll to the second storage roll.

15. A method of inspecting a characteristic of a flexible glass ribbon, the method comprising the steps of:
   (I) providing a first storage roll storing a first length of the flexible glass ribbon;
   (II) guiding an unrolled portion of the flexible glass ribbon with a plurality of rollers as the glass ribbon travels along a travel path of the flexible glass ribbon;
   (III) moving a first roller of the plurality of rollers closer to or farther away from a second roller of the plurality of rollers to adjust a tension in an inspection region of the unrolled portion of the flexible glass ribbon, wherein the inspection region spans between the first roller and the second roller; and
   (IV) inspecting a characteristic of a glass portion within the inspection region between the first roller and the second roller.

16. The method of claim 15, wherein step (IV) includes inspecting the characteristic comprising a stress characteristic, thickness, or warp, of the glass portion of the unrolled portion of the flexible glass ribbon.

17. The method of claim 15, wherein step (IV) includes operating an optical device to inspect the characteristic of the glass portion of the unrolled portion of the flexible glass ribbon.

18. The method of claim 15, wherein step (IV) includes exposing the glass portion of the unrolled portion of the flexible glass ribbon with polarized light while at least one camera inspects the characteristic comprising a stress characteristic of the glass portion of the unrolled portion of the flexible glass ribbon.

19. The method of claim 15, wherein step (IV) includes inspecting an elongated member relative to the unrolled portion of the flexible glass ribbon with at least one camera to inspect a warpage of the glass portion of the flexible glass ribbon.

20. The method of claim 15, further comprising storing a second length of the flexible glass ribbon with a second storage roll, and step (IV) is carried out while the unrolled portion travels along the travel path from the first storage roll to the second storage roll.

* * * * *